United States Patent
Carr, Jr. et al.

[11] Patent Number: 5,997,896
[45] Date of Patent: Dec. 7, 1999

[54] RECONSTITUTED COLLAGEN FIBER SEGMENT COMPOSITIONS AND METHODS OF PREPARATION THEREOF

[75] Inventors: Robert M. Carr, Jr., West Roxbury, Mass.; John F. Cavallaro, Hanover, N.H.; Lisa M. Bryant, Quincy; David W. Donovan, Somerville, both of Mass.; Paul D. Kemp, Romiley, United Kingdom

[73] Assignee: Organogenesis, Inc., Canton, Mass.

[21] Appl. No.: 08/973,571

[22] PCT Filed: Jun. 7, 1996

[86] PCT No.: PCT/US96/09861

§ 371 Date: May 11, 1998

§ 102(e) Date: May 11, 1998

[87] PCT Pub. No.: WO96/40216

PCT Pub. Date: Dec. 19, 1996

Related U.S. Application Data

[63] Continuation-in-part of application No. 08/483,092, Jun. 7, 1995, abandoned.

[51] Int. Cl.$^6$ .......................................................... A61F 2/02
[52] U.S. Cl. ................................................................. 424/426
[58] Field of Search ............................................... 424/426

[56] References Cited

U.S. PATENT DOCUMENTS 5,475,052  12/1995  Rhee et al. ........................... 525/54.2

*Primary Examiner*—Carlos Azpuru
*Attorney, Agent, or Firm*—Hale and Dorr LLP

[57] ABSTRACT

The invention provides injectable collagen compositions that are reconstituted collagen fiber segments made from acid extracted collagen with telopeptides in a biocompatible carrier, with the collagen concentration in the composition ranging up to 200 mg/mL.

20 Claims, 1 Drawing Sheet

RECONSTITUTED COLLAGEN FIBER SEGMENT COMPOSITIONS AND METHODS OF PREPARATION THEREOF

This application is a rule 371 continuation of PCT/US96/09861 filed Jun. 7, 1996. This application is also a continuation-in-part of U.S. Ser. No. 08/483,092 filed Jun. 7, 1995, now abandoned.

FIELD OF INVENTION

The invention relates to collagen fiber segments, to methods for production of such collagen fiber segments, and to articles of manufacture incorporating such collagen fiber segments, for example, injectable collagen compositions for tissue augmentation and drug delivery.

BACKGROUND OF THE INVENTION

Collagen is the principal structural protein in the body and constitutes approximately one-third of the total body protein. It comprises most of the organic matter of the skin, tendons, bones and teeth and occurs as fibrous inclusions in most other body structures. Some of the properties of collagen are its high tensile strength; its ion exchanging ability, due in part to the binding of electrolytes, metabolites and drugs; its low antigenicity, due to masking of potential antigenic determinants by the helical structure, and its low extensibility, semipermeability, and solubility. Furthermore collagen is a natural substance for cell adhesion. These properties and much more make this protein suitable for fabrication into medical products such as in the manufacture of implantable prostheses, as cell growth substrates, and in the preparation of cellular and acellular tissue equivalents.

Collagen compositions are typically prepared from skin or tendons by dispersion, digestion or dissolution. Dispersion involves mechanically shearing the tissue to produce a suspension of collagen fibers. Digestion involves enzyme degradation of the non-helical telopeptide portions of the collagen molecule, resulting in a solution of atelopeptide collagen. Dissolution involves cleavage of acid labile crosslinks in newly formed collagen fibers resulting in a solution of collagen monomers and polymers. procedures involving acid or enzyme extraction. Enzyme extraction is preferable in many instances because its methodology produces increased yield and higher purity collagen. However enzyme extraction suffers the disadvantage of producing partially degraded collagen, i.e., the extraction enzymes cleave the collagen molecule at the terminal non-helical regions which contain the inter-molecular cross-linkages.

Injectable formulations have been used in the art as tissue bulking compositions, particularly in urology and plastic surgery. U.S. Pat. No. 3,949,073 to Daniels et al discloses an injectable collagen in aqueous form composed of enzyme extracted collagen. The enzyme used in the extraction process is pepsin which yields atelopeptide collagen. The concentration of the final product is up to about 20 mg/mL but insoluble collagen fibrils may also be added to the composition. Upon implantation to a patient, however, the volume persistence of the implant decreases partly due to the absorption of the aqueous carrier by the body and partly due to the low concentration of the collagen. Follow up injections at the site are usually necessary.

Volume persistence and shape persistence desired of the injected collagen implant In the time after injection of collagen compositions known in the art, the volume decreases due to the absorption of liquid component of the composition by the body. Higher concentrations of collagen helps to maintain volume persistence, but at the same time decreases extrudability and intrudability of the composition.

U.S. Pat. No. 4,642,117 to Nguyen et al discloses an injectable collagen material composed of reconstituted, mechanically sheared atelopeptide collagen fibers. The collagen fibers are mechanically sheared using a rigid screen mesh to reduce the size of the larger fibers to about 50–150 microns. The disclosed composition has a final concentration of about 35–65 mg/mL, but it was determined that the extrudability and intrudability are poor. U.S. Pat. No. 4,582,640 to Smestad describes a similar composition that is glutaraldehyde crosslinked. In clinical testing, however, it was found that the intrudability of the composition was also difficult, especially for intradermal injections. U.S. Pat. No. 4,803,075 to Wallace et al discloses a similar injectable compositions with the addition of a biocompatible fluid lubricant to overcome the problems of extrudability and intrudability.

As well as volume persistence, shape persistence is desired of the injectable collagen compositions know in the art. When injected, the collagen tends to migrate through the tissue; therefore, if specific and local tissue augmentation or bulking is required, such migration would necessitate subsequent injections.

The present invention describes a collagen composition in the form of reconstituted collagen fiber segments, methods for making collagen fiber segments and their use as an injectable collagen composition that overcomes the drawbacks of injectable collagen compositions known in the art.

SUMMARY OF THE INVENTION

The invention provides collagen fiber segments and injectable collagen compositions comprising collagen fiber segments and methods for making and using such collagen fiber segments.

The present invention provides injectable collagen compositions having improved properties over known injectable collagen compositions in the art. Preferred injectable collagen compositions prepared in accordance to the present invention have a high concentration of collagen; The injectable compositions are useful for tissue augmentation, tissue repair and drug delivery. They also have unproved characteristics for bioremodeling than other known compositions.

DETAILED DESCRIPTION OF THE INVENTION

Figure 1:
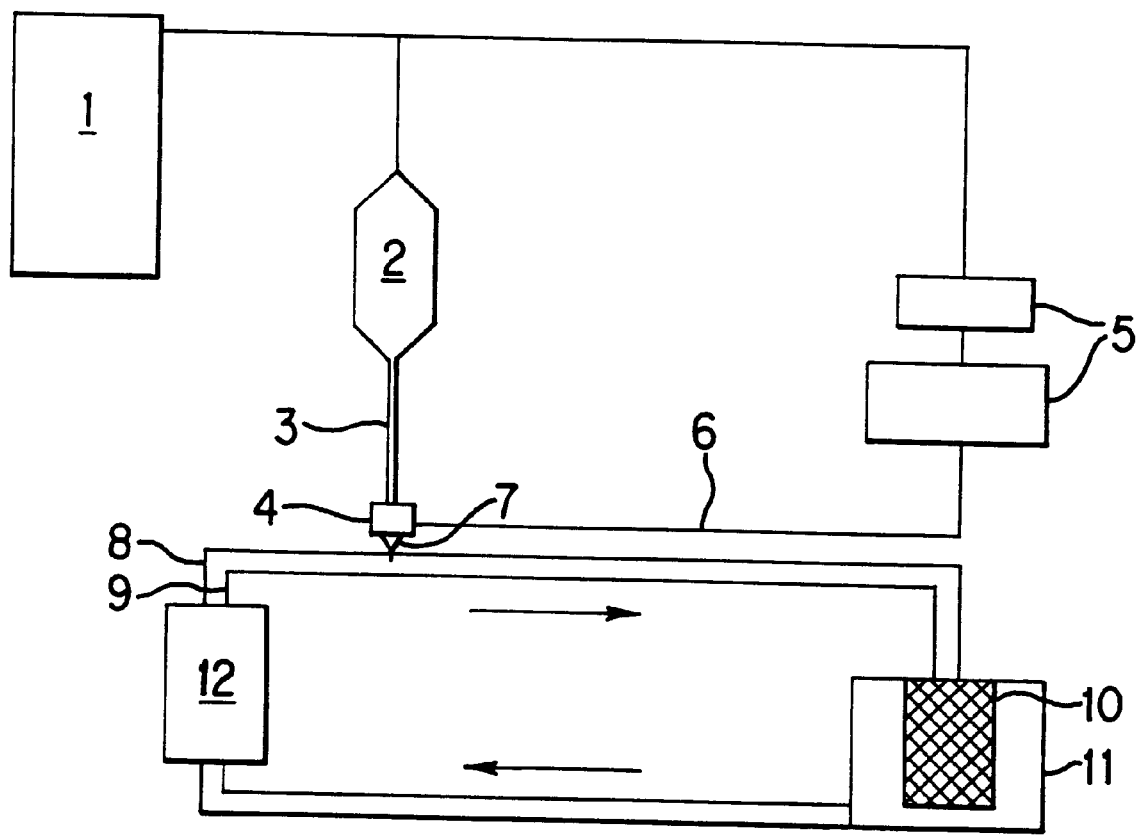
FIG. 1 is a schematic representation of one apparatus for use in the methods to produce reconstituted collagen fiber segments.

Collagen for use in the present invention may be obtained from any suitable source, typically skin and tendons. Many procedures for obtaining and purifying collagen, typically involving acid or enzyme extraction, are known to practitioners in the art and may be used to prepare collagen for use in the present invention. Collagen obtained using acid extraction methods is more preferable over enzyme extraction methods as the non-helical telopeptide regions are maintained in the collagen molecule when acid extraction methods are used. A preferred collagen composition for use in the present invention is acid extracted bovine tendon collagen, disclosed in U.S. Pat. No. 5,106,949, incorporated herein by reference.

Collagen solutions comprising collagen for making collagen thread segments by the methods described herein are generally at a concentration preferably of at least about 1 mg/L to about 10 mg/mL, more preferably from about 4 mg/mL to about 6 mg/mL, most preferably at 4.5 to 5.5 mg/mL, and at a pH of about 2 to 4. A preferred solvent for the collagen is dilute acetic acid at about 0.05 to 0.1%, more preferably at about 0.05%. Other dilute acid solvents that can be used are hydrochloric acid, citric acid, and formic acid. The collagen solution may optionally have substances such as pharmaceuticals; growth factors; hormones; other extracellular matrix components; other collagen types; or genetic material; such as vectors or other genetic constructs, or antisense oligonucleotides, or the like, included in the solution. When collagen fiber segments are formed with these substances in the collagen solution, these substances will be incorporated in the segments.

In a preferred methods of the present invention, collagen fiber segments are made by a methods comprising: discontinuously extruding a solution comprising collagen into a neutralizing and/or dehydration agent, sometimes termed 'coagulation agent', the agent capable of neutralizing and/or dehydrating the collagen solution to form collagen fiber segments; and collecting the formed collagen fiber segments.

The dehydration agent should be a solution that will remove the water from the collagen solution so that the collagen is concentrated. When the collagen concentrates, it becomes more solid. One preferred dehydration bath comprises a dehydrating agent having a higher osmotic pressure than that of the collagen solution, preferably higher than about 500 mOsm and a pH from about 5 to 10, with a pH of about 7 to 9 preferred. Other preferred dehydrating agents include water soluble, biocompatible polymers such as DEXTRAN® and polyethylene glycol (PEG). Salt solutions such as phosphate buffered saline (PBS) are preferred wherein the phosphate is at a concentration from about 0.001 to about 0.02 M and a salt concentration from about 0.07 to about 0.3 M. Other preferred dehydration agents are isopropyl alcohol and acetone. In the preferred embodiment, 20% w/v polyethylene glycol, MW 8000 (PEG-8000), in phosphate buffer is used.

The collagen solution is dispensed in small quantities from a containing reservoir. The means for dispensing can be made manually using a syringe or automatically controlled using a pump attached to a syringe or cartridge containing the collagen solution.

In other preferred methods of the present invention, the method of making collagen fiber segments further comprises rinsing the formed fiber segments in a buffer to remove residual dehydration/neutralizing agent.

It may be additionally desirable to crosslink the collagen fiber segments. Crosslinking provides strength to the collagen fibers and regulates bioremodeling of the collagen by cells when implanted into a patient. Although crosslinking may be carried out without rinsing the collagen fiber segments, in preferred embodiments the collagen fiber segments are rinsed prior to crosslinking.

As used herein, the term collagen fiber segments is therefore intended to mean processed collagen, prepared from collagen solutions, such that it is reconstituted as a fiber segment.

For the purpose of illustrating preferred embodiments of the invention only, and not for the purpose of limiting the same, the methods of the present invention will be illustrated by preparing collagen fiber segments by means of the apparatus shown in FIG. 1.

FIG. 1, includes a compressed air source 1 connected to a reservoir cartridge 2, high pressure tubing 3, a dispensing valve 4, and a needle 7 inserted through tubing 8. The compressed air source 1 is also connected to a pneumatic controller 5, and the a dispensing valve 4 through a tubing 6. The neutralizing and dehydrating bath 9, is connected to a peristaltic pump 12, and a flask with an outlet located at its base 11, containing mesh bag 10, through a tubing 8.

In one preferred embodiment, a cartridge containing collagen at 5 mg/mL in 0.05% acetic acid 2, is placed under constant pressure by compressed air supplied by a regulated air pressure source 1. The collagen is released from the dispensing valve 4, through a high pressure tubing 3. The valve 4 is joined to a pneumatic controller 5, through a tubing 6, which provides repeated pulses of air to the valve 4. The valve 4 is fitted with a blunt tipped needle 7, positioned in the wall of the tubing 8 so that the tip is located about center of the lumen. The tubing 8 forms a recirculated neutralizing and/or dehydration bath 9 which was recirculated by use of a peristaltic pump 12, at a rate of about 520 mL/min. The recirculated bath 9, serves to neutralize and dehydrate the collagen solution to form collagen fiber segments. In the circuit, downstream of dispensing needle 7, a flask 11 containing a porous bag 10, fastened in-line of the recirculated bath within the flask 11 at the end of the tube. The circuit continues from the outlet at the base of the flask to the peristaltic pump 12, to create the flow of the bath, and back to the dispensing needle 7.

The collagen, under pressure in the reservoir cartridge 2, is released from the dispensing valve 4, through the needle 7, to the recirculating bath 9, in incremental amounts when air is discharged in pulses from the controller 5 to the dispensing valve 4. The rate of the flowing bath 9 is regulated so that the released collagen was pulled into a roughly cylindrical segment. When the collagen release is stopped, the segments are sheared from the needle tip 7, and are carried by the recirculating bath 9, to the flask 11, containing the porous bag 10. The segments are captured by the porous bag 10, while the bath 9, passes through the bag to the outlet at the bottom of the flask 11, to the outlet and into the circuit.

Preferred materials for the apparatus described are compatible with collagen fiber formation, the desired properties of the collagen fiber and the materials used in collagen fiber formation. In some instances, the apparatus must be capable of withstanding sterilization. Modifications to the apparatus and the method may be made to still produce collagen fiber segments.

In another embodiment, the dispension control is administered by directly imparting pressure to the syringe plunger in increments. In yet another embodiment the syringe plunger is absent and control is administered by directly imparting pulses of air to the collagen solution contained in the syringe cartridge. However, the valve control is preferred as it allows for consistency and regulation in the dispensing of the solution. Other means of controlling the release of small amounts of collagen solution may be employed by those skilled in the art.

From the tube leading from the cartridge, if no valve is used, or from the valve, a short conduit for introducing the dispensed collagen solution to a dehydration bath is attached thereto. The conduit should have at least one orifice and is preferably a blunt tipped needle or similarly shaped. The gauge of the needle or orifice is preferably between 12 to 30 gauge, more preferably 14 to 21 gauge. The shape of the orifice may be round, oblong or any other shape. An oblong shaped orifice will yield ribbon-like collagen fiber segments. The orifice is preferably submerged in the dehydration bath but may also be in the area above the bath so that the solution is dropped into the bath. When the orifice is submerged, the shape of the collagen fiber segments formed are more easily controlled. Other means known in the art for delivering collagen solution to the dehydration bath may be employed. Modifications of the apparatus and the method may be made by the skilled artisan to obtain effectively the same result.

The dehydration bath 9, relative to the dispensing orifice 7, should be in motion. The speed of the dehydration bath relative to the rate the collagen solution is released from the orifice determines the shape of the formed collagen fiber segments. Slower baths will form segments that are spherical or comma shaped. At the similar rates, a generally cylindrical shape will be formed. Faster bath rates will form elongated fibers with tapered ends. The speed of the bath can be adjusted according to the desired fiber shape.

The dehydration bath of the present invention is a preferably a closed circuit to maintain sterility of the product. Size 17 NEOPRENE tubing is used but any tubing may be used. An open bath could substituted by interchanging the tubing for troughs or other conduits for conducting liquids.

The collection filter should have apertures small enough as to not allow for the passage of the collagen fiber segments but large enough to allow for the flow of the bath. A nylon mesh bag containing apertures of 250 $\mu$m attached to the tubing and enclosed within a flask is used but any collection vessel with a filter and an outlet may be substituted.

The bath is recirculated by use of a peristaltic pump situated upstream from the dispensing needle. Any pumping means may be substituted, preferably one that maintains sterility of the system.

Collagen fiber segments that have been collected in the bag after removal from the flask are rinsed, if preferable, with purified water or with phosphate buffered saline. Rinsing will remove any residual neutralizing and/or dehydration agents that may remain on the material.

The nature of the collagen fiber segments will depend upon the following variables: the collagen concentration; the orifice through which the collagen is extruded; the rate of which the collagen is extruded; the volume of collagen solution extruded in each pulse; and the rate of circulation of the bath. The maximum concentration of collagen in a wet thread is about 325 mg/mL. The collagen concentration range of the final product depends upon the volume ratio of collagen fiber segments and surrounding liquid. By altering the above variables, collagen fiber segments have been produced ranging from 0.05 to 2.5 mm in diameter and at least 2 mm in length. Moreover, truncated segments could be produced by mechanical homogenization of the threads. The skilled artisan would be able to alter the parameters to produce collagen fiber segments of other dimensions.

The collagen fiber segments are then optionally crosslinked with a crosslinking agent. Collagen crosslinking agents include glutaraldehyde, formaldehyde, carbodiimides, hexamethylene diisocyanate, bisimidates, glyoxal, polyglycerol polyglycidyl ether, adipyl chloride, dehydrothermal, UV irradiation and sugar-mediated. Collagen will also naturally crosslink with age standing at room temperature. However, crosslinking agents need not be limited to these examples as other crosslinking agents and methods known to those skilled in the art may be used. Crosslinking agents should be selected so as to produce a biocompatible material capable of being remodeled by host cells. A preferred crosslinking agent is 1-ethyl-3-(3-dimethylaminopropyl) carbodiimide hydrochloride (EDC). The crosslinking solution containing EDC and water may also contain acetone.

The collagen fiber segments can also be sterilized in a dilute peracetic acid solution with a neutral pH. Methods for sterilizing collagen are described in U.S. Ser. No. 08/177,618, now U.S. Pat. No. 5,460,962 and are incorporated by reference herein.

The collagen fiber segments may also be coated with agents such as pharmaceuticals; growth factors; hormones; other extracellular matrix components; or genetic material. Coating of the agent can be achieved by immersion or chemical binding. Cells may be cultured on the segments as collagen is a natural substrate for cells to bind.

The collagen fiber segments, to be used as an injectable composition, are transferred to a syringe. Injectable preparations have been made ranging up to 200 mg/mL collagen in isotonic saline. Other biocompatible carriers may be substituted for isotonic saline by one skilled in the art.

The collagen fiber segments may be used for surgical procedures for implantation to a patient. Indications for a collagen implant are for tissue augmentation, tissue repair, or drug delivery. Collagen implants are used for adding tissue bulk to sphincters, such as an urinary sphincter, or for cosmetic surgery. Tissue repair is achieved by providing the composition to an area of tissue that has been diseased, wounded or removed. Drugs are delivered to enhance tissue repair or as therapeutic agents when they are added to the composition. Incorporation of cells to the collagen fiber segments provides a means for delivering cells to repopulate a damaged or diseased tissue area or to provide cell synthesized products to the surrounding tissues.

Delivery of the implant may be done manually by depositing an amount of collagen fiber segment composition between tissues or to bridge a gap or defect in a single tissue. A preferred means of delivery is by injection with the use of a syringe. The concentration of collagen in the composition is dependent on the indication. The addition of other components and other terminal treatments to the collagen fiber segment composition may alter the concentration of the final composition.

In another preferred method for making collagen fiber segments, controlled mixing of a collagen solution with coagulation agent is performed. Controlled mixing was obtained by use of a rotating shaker platform, a stirbar on a magnetic stirrer, or a kitchen blender. Other means to controllably mix a volume liquid will appreciated and determined by those skilled in the art. In the preferred method, a device resembling a typical kitchen blender, with some modifications to the speed controller and blades, is used. Modifications to the speed controller allows the mixing to be performed at speeds not offered by the standard apparatus. The blades of the blender are covered with tubing to round the edges of the blender chopping blade so as to eliminate the cutting of the formed collagen fiber segments during controlled mixing. Alternatively, the chopping blades could be replaced with mixing paddles or other means known by the skilled artisan to produce the desired forces.

To the chamber of the blender is added a volume of dehydration and/or neutralizing agent. The blender is then activated to mix the agent at a desired rate. Collagen solution of preferably at least 1 mg/mL in dilute acetic acid is then poured into the mixing agent. The collagen and agent are then allowed to mix for a time sufficient for the collagen solution to coagulate by dehydration and/or neutralization to form collagen fiber segments. Once formed, the blender is turned off and the admixture is allowed to stand for a time to allow the collagen fiber segments to set. To remove the fiber segments from the agent, the mixture is centrifuged or filtered. Using centrifugation, the mixture is decanted into centrifuge tubes so that the fiber segments form a pellet and the agent, the supernatant, is poured off. The fiber segments are preferably rinsed, also by employing centrifugation method, by resuspending the fiber segments in water or buffered saline and again centrifuging to pellet the fiber segments. The rinse step may be repeated as necessary. Subsequent crosslinking steps with a crosslinking agent may also be performed using the centrifugation method. Pellets are resuspended in crosslinking agent, preferably EDC in water and acetone, to contact crosslinking agent to the collagen fiber segments. After the crosslinking reaction has been has been carried out, the rinse step is preferably repeated to remove excess crosslinking reagent and reaction by-products. Other means for removing dehydration agent, rinsing and crosslinking collagen fiber segments can be determined by one skilled in the art. Once the collagen fiber segments have been prepared, they can be diluted after any centrifugation step to an extrudable and intrudable concentration.

Collagen fiber segments prepared by the method controlled mixing of a collagen solution with coagulation agent are from about 0.001 mm to about 20 mm in length, more preferably between 0.1 to 2.0 mm in length. In collagen fiber segments formed using the controlled mixing method, segments of lengths greater than 1 mm tend to have a branched or forked structure.

Another further embodiment to make collagen fiber segments is one where collagen threads are chopped or homogenized. Injectable collagen compositions are also made from homogenized collagen thread. Methods for preparing collagen thread are disclosed in U.S. Pat. No. 5,378,469, incorporated herein by reference. A solution of 5 mg/mL acid extracted bovine tendon collagen is extruded into a neutralizing and/or dehydrating agent having a higher osmotic pressure than that of the collagen solution and a pH of about 5 to 9 and the neutralizing and/or dehydrating agent is maintained under conditions to enable collagen thread formation. The thread may optionally be crosslinked. The thread is then transferred to a culture tube with purified water added to wet the threads. A tissue homogenizer is used to mince the threads into small collagen fiber segments. The mixture is placed in a funnel with a filter to remove excess water. The collagen fiber segments thus formed can be used as injectable composition by transferring into a syringe. Other methods of mincing and chopping threads into collagen fiber segments may be employed, for example, cutting or chopping.

The following examples are provided to better elucidate the practice of the present invention and should not be interpreted in any way to limit the scope of the present invention. Those skilled in the art will recognize that various modifications, can be made to the methods described herein while not departing from the spirit and scope of the present invention.

EXAMPLES

Example 1

Production of Collagen Fiber Segments by Pulsed Extrusion Method Using a Dispensing Valve A cartridge containing collagen at 5 mg/mL in 0.05% acetic acid was placed under constant pressure by compressed air at 20 psi (138 kPa) supplied by a regulated pressured air source. A tube was connected that allowed collagen to flow to an EFD 752 dispensing valve (EFD, E. Providence, R.I.). At the valve was also joined a tube leading from an EFD 900 pneumatic controller with a switch, also provided with air under constant pressure of 80 psi (552 kPa), which provided repeated pulses of air to the valve. The valve was fitted with a 21 gauge blunt tipped needle that pierced the wall of size 17 NEOPRENE tubing with the needle tip approximately centered within the lumen of the tubing. The tubing formed a circuit of 20% polyethylene glycol MW 8000 (PEG-8000) in phosphate buffer at pH 7.6 (w/v) which was recirculated by use of a peristaltic pump at a rate of about 200 mL/min. The PEG bath served to neutralize and dehydrate the collagen solution to form collagen fiber segments. In the circuit, downstream of dispensing needle, a vacuum flask is connected at its mouth with a stopper and tubing therethrough with a 250 micron porous nylon bag fastened within the flask at the end of the tube. The circuit continued from the outlet at the base of the flask to a peristaltic pump, to create the flow of the bath, and back to the dispensing needle.

Collagen solution, under pressure, was released from the dispensing valve, through the needle, to the recirculating bath in incremental amounts when amounts of air are discharged in pulses from the dispenser. The rate of the flowing bath was regulated so that the released collagen was pulled into a roughly cylindrical segment. When the collagen release was stopped, the segments were sheared from the valve tip and were carried by the recirculating bath to the flask containing the porous bag. The segments were captured by the porous bag while the PEG bath passed through the bag to the bottom of the flask to the outlet and into the circuit. When a number of collagen fiber segments had been collected in the bag, the bag was removed from the flask.

Example 2

Production of Collagen Fiber Segments by Pulsed Extrusion Method

An alternate apparatus assembly was used to produce collagen fiber segments by pulsed extrusion method.

An EFD 900 pneumatic controller and dispensing system was provided with air under constant pressure at 50 psi (345 kPa) supplied by a regulated pressured air source. The controller and dispensing system provided repeated pulses of air by a tube to a 30 cc syringe cartridge containing acid extracted collagen at 5 mg/mL in 0.05% acetic acid. From the cartridge was a tube fitted at the end with a 30 gauge blunt tipped needle that pierced the wall of size 17 NEOPRENE tubing with the needle tip approximately centered within. The tubing formed a circuit of 20% polyethylene glycol MW 8000 (PEG-8000) in phosphate buffer at pH 7.6 (w/v) which was recirculated by use of a peristaltic pump at a rate of about 520 mL/min. The PEG bath served to neutralize and dehydrate the collagen solution to form collagen fiber segments. In the circuit, downstream of dispensing needle, a vacuum flask is connected at its mouth with a stopper and tubing therethrough with a 250 micron nylon mesh bag fastened within the flask at the end of the tube. The circuit continued from the outlet at the base of the flask to a peristaltic pump, to create the flow of the bath, and back to the dispensing needle.

The cartridge containing collagen solution received pulses of compressed air to force collagen, in incremental amounts, from the cartridge and out through the needle to the recirculating dehydration bath. The rate of the flowing bath was regulated so that the released collagen was pulled into a roughly cylindrical segment. When the collagen release was stopped, the segments were sheared from the needle tip and were carried by the recirculating bath to the flask containing the porous bag. The segments were captured by the porous bag while the PEG bath passed through the bag to the bottom of the flask to the outlet and into the circuit. When a number of collagen fiber segments had been collected in the bag, the bag was removed from the flask.

Example 3

Production of Collagen Fiber Segments by Pulsed Extrusion Method into Other Dehydration Compositions Using the apparatus assembly of Example 2, collagen fiber segments were formed by pulsed extrusion method into other compositions with qualities that enable collagen fiber formation.

At separate times, the PEG-8000 dehydration bath was replaced with either isopropanol or acetone. The collagen fiber segments were formed by the method of Example 2 and were collected in the porous bag while either the isopropanol or acetone bath passed through the bag to the bottom of the flask to the outlet and into the circuit. When a number of collagen fiber segments had been collected in the bag, the bag was removed from the flask.

Example 4

Production of an Injectable Collagen Composition of Collagen Fiber Segments Prepared by Pulsed Extrusion Method For preclinical evaluation, a number of compositions comprising collagen were prepared to study bioremodeling of the collagen. Either the collagen solution used to make the collagen fiber segments was varied or the formed collagen fiber segments were further treated after formation.

Composition 1 was a composition of collagen fiber segments, prepared by the method of Example 2, using 5 mg/mL acid extracted bovine tendon collagen. The collagen fiber segments were rinsed in purified water.

Composition 2 was a composition of crosslinked collagen fiber segments. Collagen fiber segments were prepared by using the apparatus and method of Example 2 using 5 mg/mL acid extracted bovine tendon collagen. After rinsing the collection bag containing the fiber segments with purified water, the fiber segments were crosslinked by submerging the bag in 5 mM EDC in water for 4 hours.

Composition 3 was a composition where the collagen fiber segments were constructed from partially heat denatured collagen. Before loading the cartridge, 5 mg/mL acid extracted bovine tendon collagen was denatured by heating at 50° C. for thirty minutes. Denatured collagen was mixed with non-denatured 5 mg/mL acid extracted bovine tendon collagen at a 1:1 ratio to form a partially denatured collagen mixture. Partially denatured collagen fiber segments were prepared using the apparatus and method of Example 2. The collagen fiber segments were rinsed in purified water.

Composition 4 was a composition of collagen fiber segments prepared from enzyme extracted collagen. Pepsin extracted collagen at 6.7 mg/mL (Pentaphanm, Basel, Switzerland) was used as the collagen solution from which collagen fiber segments were formed according to the method of Example 2.

Composition 5 was a composition of collagen fiber segments prepared from human collagen produced from cultured cells. The method for obtaining collagen from cultured cells is described in U.S. Ser. No. 08/240,516 and is incorporated herein. The human collagen at 5 mg/mL was used as the collagen solution from which collagen fiber segments were formed according to the method of Example 2.

Compositions 1, 2 and 3 were sterilized by placing the bags containing the collagen fiber segments in 0.1% neutralized peracetic acid in phosphate buffered saline for sixteen hours and were finally rinsed in sterile phosphate buffered saline. Collagen concentrations of the compositions were determined. The final concentration of Composition 1 was 69.4 mg/mL. The final concentration of Composition 2 was 88.8 mg/mL. The final concentration of Composition 3 was 88.1 mg/mL.

Example 5

Production of an Injectable Collagen Composition of Collagen Fiber Segments By Homogenization Composition 6 was made of collagen thread using 5 mg/mL acid extracted bovine tendon collagen. Methods for preparing collagen thread are disclosed in U.S. Pat. No. 5,378,469. An amount of dry age-crosslinked thread weighing 1.0 g was cut into small pieces with scissors. The threads were transferred to a culture tube and 10 mL of purified water was added to wet the threads. A tissue homogenizer was used at high speed for two minutes to mince the thread to a paste consistency with a concentration of about 150 mg/mL. The mixture was placed in a funnel with a filter to remove excess water for approximately ten minutes and then stored at 4° C.

Composition 7 was made of collagen thread using 5 mg/mL acid extracted bovine tendon collagen, also by methods disclosed in U.S. Pat. No. 5,378,469. An amount of dry thread weighing 1.0 g was cut into small pieces with a razor blade. The threads were transferred to a culture tube and 10 mL of purified water was added to wet the threads. The mixture was placed in a funnel with a filter to remove excess water for approximately ten minutes and then stored at 4° C.

Example 6

Incorporation of TGFβ to Collagen Fiber Segments

The use of collagen fiber segments for drug delivery was investigated. Collagen fiber segments were incorporated with radiolabelled [$I^{125}$] TGFβ (Collaborative Research) by two methods: by surface coating the formed collagen fiber segments with [$I^{125}$] TGFβ; or by forming the collagen fiber segments with [$I^{125}$] TGFβ incorporated within.

Collagen fiber segments were prepared by the method of Example 2. A total of 10 mL of collagen solution at 5 mg/mL in 0.05% acetic acid was used. The bag containing collagen fiber segments were removed from the flask. To surface coat the collagen fiber segments, the collagen fiber segments were removed from the bag and were then immersed in 0.8 μCi of [$I^{125}$] TGFβ overnight at 4° C.

Collagen fiber segments were also formed with TGFβ incorporated within. To 10 mL collagen solution at 5 mg/mL in 0.05% acetic acid was added 0.8 μCi of [$I^{125}$] TGFβ and mixed. Collagen fiber segments also were formed by the method of Example 2.

Elution studies of the [$I^{125}$] TGFβ were performed on about 100 mg aliquots, in triplicate, of the two treatments. Each aliquots of collagen thread segments was immersed in 5 mL of 0.4% bovine serum albumin (BSA) in phosphate buffered saline (PBS) and mixed on a shaker platform at 37° C. The radioactivity of the BSA/PBS was measured at timepoints ranging from 2 to 500 hours.

Results of the elution study show that collagen fiber segments coated with [$I^{125}$] TGFβ elute the radiolabelled growth factor faster than the collagen fiber segments formed with [$I^{125}$] TGFβ incorporated within.

Example 7

Pre-Clinical Study of Injectable Collagen Composition of Collagen Fiber Segments By Pulsed Extrusion Method An animal model was used to prove safety and efficacy of the injectable compositions. New Zealand white rabbits were chosen as an animal model due to the large surface area of the ears for subcutaneous injection of the compositions. Eleven rabbits were used in the study.

Compositions 1, 2, and 3, as prepared in Example 4, were aseptically loaded into a number of 3 cc syringes with 0.5 mL of composition per syringe. As a comparison, CONTIGEN (Bard, Billerica, Mass.), an afibrillar suspension of pepsin extracted glutaraldehyde crosslinked bovine dermal collagen at 35 mg/mL was also used.

All rabbits were tattooed with an arrangement of black dots to record the sites of injection, and to provide control points for measuring ear growth and persistence of the injected composition. Prior to tattooing, all animals were anesthetized with 20 cc ace promazine (Schein). Tattoos were allowed to heal for 26 days prior to collagen injections to ensure that all inflammation due to tattoos had subsided.

All collagen injections were performed using aseptic technique. All animals were anesthetized using 0.3 mL of 100 mg/mL xylazine (Miles) and 3.0 mL of 100 mg/mL ketamine (Fort Dodge) prior to injections. For implants the animals were given 0.5 mL of compositions subcutaneously through a 1-inch 18 G needle.

Tattoo point measurements were taken at 0, 2, 4, 7, 10, 14, 21 days and every seven days thereafter for the duration of the study. All tattoo points were measured with a micrometer and results recorded in millimeters. Rabbits were sacrificed at 6 weeks and 12 weeks using 0.3 mL of 100 mg/mL xylazine (Miles) and 3.0 mL of 100 mg/ml ketamine (Fort Dodge), plus 5 cc of 1.5 M KCl (Sigma). Following sacrifice, all ears were dissected to free excess skin around implant and were fixed in formalin for 24 hours before processing for histology.

Compositions 1, 2, and 3 remained localized at the injection site whereas CONTIGEN spread through the tissue upon injection.

Example 8

Collagen Fiber Segments Produced by Controlled Mixing of Collagen Solution with Coagulation Agent A suspension of collagen fiber segments was prepared by controlled mixing of a collagen solution with coagulation agent. Controlled mixing was obtained by use of a kitchen blender (Oster) modified with a voltage controller (Variac). The voltage controller allowed for variable speeds to be obtained that were not possible with the standard speeds offered by the apparatus. The blades of the blender were each modified by covering the length of the blades with Neoprene tubing.

A 400 mL volume of 8000 MW polyethylene glycol (PEG-8000) solution (20% PEG-8000 in phosphate buffer, pH 7.6–7.8) was added to the blender chamber and the blender was turned on to create a turbulent vortex of dehydration agent. A 200 mL volume of collagen at a concentration of 1 mg/mL, in 0.05% acetic acid was then added to the blender chamber, the addition being completed within about 10 seconds. The admixture was allowed to mix for about 60–70 seconds and was then stopped and the mixture was allowed to stand for about 4 to 5 minutes. The mixture was then transferred into centrifuge tubes, and centrifuged at about 1000×g for about 4 to 5 minutes. The supernatants were decanted and discarded. Each tube was then filled with purified water, shaken briefly and centrifuged again for another about 4 to 5 minutes. The pellets were then pooled and the purified water rinse step repeated. The supernatants were then discarded and a volume of PBS was added to suspend the pelleted segments in the desired concentration.

Example 9

Pre-Clinical Study of Injectable Collagen Compositions of Collagen Fiber Segments Produced by Controlled Mixing of Collagen Solution with Coagulation Agent An animal model was used to prove safety and efficacy of injectable compositions prepared by the method of Example 8. New Zealand white rabbits were chosen as an animal model due to the large surface area of the ears for subcutaneous injection of the compositions. Ten rabbits were used in the study.

Non-crosslinked compositions of 33.3, 55.1 and, 58.6 mg/mL and a 5 mM EDC crosslinked composition of 58.6 mg/mL were aseptically loaded into a number of 3 cc syringes with 0.5 mL of composition per syringe.

All collagen injections were performed using aseptic technique. All animals were anesthetized based on body weight, using 10 mg/kg of 100 mg/mL xylazine (Miles), 40 mg/kg of 100 mg/mL ketamine (Fort Dodge), and 0.4 mg/kg acepromazine maleate (Henry Schein) prior to injection of collagen. For implants the animals were given 0.5 mL of compositions subcutaneously through a 1-inch 20 gauge needle.

Measurements were taken at 0, 1, 7, 21 days and every 21 days thereafter for the duration of the study. Injection thicknesses were measured with a thickness gauge and injection widths were measured using a caliper. Rabbits were sacrificed at 6 weeks and are sacrificed at 12 weeks using 0.3 mL of 100 mg/mL xylazine (Miles) and 3.0 mL of 100 mg/mL ketamine (Fort Dodge), plus 2 mL/kg of body weight of 1.5 M KCl (Sigma). Following sacrifice, all ears were dissected to free excess skin around implant and were fixed in formalin for 72 hours before processing for histology. All tested compositions remained localized at the injection site.

Although the foregoing invention has been described in some detail by way of illustration and example for purposes of clarity and understanding, it will be obvious to one of skill in the art that certain changes and modifications may be practiced within the scope of the appended claims.

What is claimed is:

1. An injectable collagen composition comprising reconstituted collagen fiber segments made from acid extracted collagen with telopeptides in a biocompatible carrier, wherein the collagen concentration in the composition may range up to 200 mg/mL.

2. The injectable collagen composition of claim 1, wherein the reconstituted collagen fiber segments are crosslinked.

3. The injectable collagen composition of claim 1, wherein the crosslinking agent is a carbodiimide.

4. The injectable collagen composition of claim 3, wherein the carbodiimide is 1-ethyl-3-(3-dimethylaminopropyl) carbodiimide hydrochloride (EDC).

5. The injectable collagen composition of claim 1, wherein the collagen fiber segments are coated with agents selected from the group consisting of pharmaceuticals, growth factors, hormones, extracellular matrix components, genetic matter and cells.

6. The injectable collagen composition of claim 1, wherein the collagen composition contains agents selected from the group consisting of pharmaceuticals, growth factors, hormones, extracellular matrix components, genetic matter and cells.

7. The injectable collagen composition of claim 1, wherein the biocompatible carrier is isotonic medium.

8. The injectable collagen composition of claim 1, wherein the reconstituted collagen fiber segments are partially denatured.

9. An injectable collagen composition comprising reconstituted collagen fiber segments made from acid extracted collagen with telopeptides, and crosslinked with a carbodiimide, in an isotonic medium, wherein the collagen concentration in the composition may range up to 200 mg/mL.

10. The injectable collagen composition of claim 1 or claim 9, wherein the reconstituted collagen fiber segments are formed by chopping reconstituted collagen threads to form reconstituted collagen fiber segments.

11. The injectable collagen composition of claim 10, wherein the chopping is achieved by homogenizing reconstituted collagen threads.

12. An injectable collagen composition comprising reconstituted collagen fiber segments made from acid extracted collagen with telopeptides in a biocompatible carrier, wherein the collagen concentration in the composition may range up to 200 mg/mL, wherein the reconstituted collagen fiber segments are formed by discontinuous extrusion of a solution comprising collagen into a recirculating bath containing an agent that dehydrates and/or neutralizes said collagen to form reconstituted collagen fiber segments.

13. The injectable collagen composition of claim 12, wherein the dehydration and/or neutralizing agent is polyethylene glycol solution.

14. The injectable collagen composition of claim 12, wherein the dehydration and/or neutralizing agent is acetone.

15. The injectable collagen composition of claim 12, wherein the dehydration and/or neutralizing agent is isopropanol.

16. The injectable collagen composition of claim 12, wherein the dehydration and/or neutralizing agent is phosphate buffered saline.

17. Reconstituted collagen fiber segments produced by the method, comprising:
   (a) discontinuously extruding a solution comprising collagen into a recirculating bath containing an agent that dehydrates and/or neutralizes said collagen, and,
   (b) maintaining said circulated bath under conditions to enable the extruded collagen to form reconstituted collagen fiber segments.

18. The method of claim 16, further comprising crosslinking said fibers.

19. The method of claim 16, further comprising coating said fibers with an agent selected from the group consisting of pharmaceuticals, growth factors, hormones, extracellular matrix components, genetic material, and cells.

20. Reconstituted collagen fiber segments produced by the method, comprising:
   (a) adding a solution comprising collagen into a controllably mixed volume of an agent that dehydrates and/or neutralizes said collagen, and,
   (b) mixing said solution comprising collagen and said agent under conditions to enable the collagen to form reconstituted collagen fiber segments.

\* \* \* \* \*